United States Patent [19]
Johnson

[11] Patent Number: 5,593,980
[45] Date of Patent: Jan. 14, 1997

[54] ARYLMETHYLPHOSPHONATES AND PHOSPHONIC ACIDS USEFUL AS ANTI-INFLAMMATORY AGENTS

[75] Inventor: Roy A. Johnson, Kalamazoo, Mich.

[73] Assignee: The Upjohn Company, Kalamazoo, Mich.

[21] Appl. No.: 556,681

[22] Filed: Nov. 13, 1995

Related U.S. Application Data

[60] Division of Ser. No. 403,229, filed as PCT/US93/08353, Sep. 10, 1993, Pat. No. 5,500,417, which is a continuation-in-part of Ser. No. 964,618, Oct. 22, 1992, abandoned, which is a continuation-in-part of Ser. No. 954,093, Sep. 30, 1992, abandoned, said Ser. No. 403,229, is a division of Ser. No. 65,056, May 20, 1993, abandoned, which is a continuation of Ser. No. 949,738, Sep. 23, 1992, abandoned.

[51] Int. Cl.$^6$ .................... A61K 31/66; A61K 31/685; C07F 9/40; C07F 9/38

[52] U.S. Cl. .................... 514/107; 514/76; 514/105; 558/162

[58] Field of Search .................... 514/107, 105

[56] References Cited

U.S. PATENT DOCUMENTS

| | | |
|---|---|---|
| 4,216,212 | 8/1980 | Flora et al. |
| 4,822,780 | 4/1989 | Tsuda et al. |
| 4,990,650 | 2/1991 | Hazato et al. |
| 5,242,908 | 9/1993 | Peyman et al. |

FOREIGN PATENT DOCUMENTS

| | | |
|---|---|---|
| WO90/12017 | 10/1990 | WIPO. |
| WO92/10504 | 6/1992 | WIPO. |

OTHER PUBLICATIONS

Lowe, N. J., et al., Brit. J. of Dermatology, 96:433–438 (1977).
Eakins, K. E., et al., Brit. J. Pharmac, 58:333–339 (1976).
Okazaki, M., et al., Chemical Abstracts, 1978, 89(3), 24537.
Otsuka Pharmaceutical Factory, Inc., Chemical Abstracts, 1986, 104(3), 19673.
Kalman, E., et al., Chemical Abstracts, 1986, 105(9), 79163y.
Database WPI, Week 8947, Derwent Publication Ltd., London, GB; AN 85–155943 & JP, A, 60 08 087 294 (Ohtsuka Seiyaku Kog) 16 May 1985.

*Primary Examiner*—Johann Richter
*Assistant Examiner*—Michael G. Ambrose
*Attorney, Agent, or Firm*—Donald L. Corneglio

[57] ABSTRACT

This invention provides a new use of acids, esters, and salts of arylmethylphosphonates of Formula I,

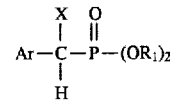

or a phosphonic acid of Formula II

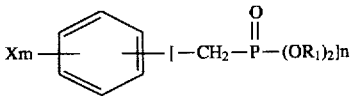

and derivatives as anti-inflammatory and anti-arthritic agents. Representative compounds include 4-dodecyloxybenzylphosphonic acid dimethyl ester, (2-naphthalenylmethyl)phosphonic acid dimethyl ester, and ([1,1'-biphenyl]-2-ylmethyl)phosphonic acid dimethyl ester.

5 Claims, No Drawings

ARYLMETHYLPHOSPHONATES AND PHOSPHONIC ACIDS USEFUL AS ANTI-INFLAMMATORY AGENTS

CROSS REFERENCE TO RELATED APPLICATION

This application is a divisional of U.S. Ser. No. 08/403,229, filed as PCT/US93/08353 Sep. 10, 1993, now U.S. Pat. No. 5,500,417, which was filed under 35 USC 371 and based on PCT/U.S.93/08353, filed Sep. 10, 1993, which is a continuation-in-part of U.S. Ser. No. 07/964,618, filed Oct. 22, 1992, now abandoned, which is a continuation-in-part of Ser. No. 07/954,093, filed Sep. 30, 1993, now abandoned; said U.S. Ser. No. 08/403,229, now U.S. Pat. No. 5,500,417 is a division of U.S. Ser. No. 08/605,056, filed May 20, 1993, now abandoned, which is a continuation of U.S. Ser. No. 07/949,738, filed Sep. 23, 1992, now abandoned.

FIELD OF THE INVENTION

This invention provides a new use of acids, esters, and salts of arylmethylphosphonate, phosphonic acids and their derivatives as anti-inflammatory and antiarthritic agents.

BACKGROUND OF THE INVENTION

Among the various phosphonate derivatives known in the art are the arylmethylphosphonates. A large number of arylmethylphosphonic acid and short-chain alkyl esters thereof, have been described. However, fewer studies describe either biochemical or pharmacological activities of these phosphonic acid derivatives. References to arylmethylphosphonates with pharmacological activity include, for example, utilities such as anxiolytic, antidepressant, calcium antagonist, anti-inflammatory, and antiviral agents, such as disinfectants, for treatment of sickle cell anemia, ischemia, hyperlipidemia, and CNS disorders.

Arylmethylphosphonates useful as anti-inflammatory and antiarthritic agents has been discovered. The arylmethylphosphonate compounds include the acids, esters, and salts thereof.

A variety of phosphonate derivatives are known in the art. However, those phenylphosphonates having three (tris) and four (tetrakis) methylenephosphonic acid groups have not been described as being useful as anti-inflammatory or antiarthritic agents.

INFORMATION DISCLOSURE

With respect to the subject invention generally, and Formula I compounds specifically, the following publications are cited.

BE 876 680 describes aralkyl and aryloxyalkyl dialkyl phosphonates having utility as topical antiviral disinfectants.

U.S. Pat. No. 4,137,309 describes diphosphonate derivatives useful for the treatment of sickle cell anemia.

EP 0 433 928 describes benzylphosphonic acids useful to treat HSV-1, HIV, and AIDS-related diseases.

U.S. Pat. No. 4,822,780 and JP 1151199 describes phosphenyl carboxylic acid amide derivatives having anti-inflammatory and calcium antagonist activity.

GB 2220206, JP 2011590, and EP 0 402 033 describe N-substituted phosphonate esters for control of hyperlipidemia and arteriosclerosis.

DE 1197882 describes sulphonated aryl phosphonates useful in the production of pharmaceuticals and as pest control agents.

U.S. Pat. No. 4,216,211 discloses phosphonates for the treatment of hypoxia and ischemic tissue disease.

U.S. Pat. No. 4,216,212 discloses phosphonates for the treatment of pain and inflammation.

DE 3736016 describes substituted alpha-amino acids as treatments for epilepsy and CNS-degenerative disorders.

None of the above references describe a use of the arylmethylphosphonate compounds of Formula I having anti-inflammatory or antiarthritic utility.

With respect to the subject invention generally, and Formula II compounds specifically, the following publications are cited.

Malkes, L. Y. and Boronenko, T. P., *Stsintill. Org. Lyuminotory* 3:42–50 (1974) as reported in *Chem. Abstr.* 86:5034z (1977) disclose the synthesis of trivinylbenzenes following reaction of aldehydes with the corresponding phosphorylated compound. No utility is reported.

Malkes, L. Y. and Kovalenko, N. P., *Zh. Organ. Khim.* 2:297 (1966) as reported in *Chem. Abstr.* 65:2188a (1966), Kovalenko, N. P., et al., *Zh. Organ. Khim.* 7:2149 (1971) as reported in *Chem. Abstr.* 76:13951e (1972), and Malkes, L. Y., et al., *Stsintill. Org. Lyuminotory* 32 (1972) as reported in *Chem. Abstr.* 83:96820e (1975) all disclose the use of 1,3,5benzenetriyltris(methylene)trisphosphonic acid, hexamethyl ester as a starting material in the formation and spectroscopic characterization of triaryl derivatives of 1,3, 5-trivinyl benzene.

Malkes, L. Y., et al., *Zh. Obsch. Khim.* 45:1481–85 (1975) as reported in *Chem. Abstr.* 83: 130829b (1975) disclose the use of [1,2,4-benzenetriyltris(methylene)]trisphosphonic acid, hexamethyl ester as a starting material in the formation and spectroscopic characterization of triaryl derivatives of 1,2,4-trivinyl benzene.

None of the latter references disclose the compounds of Formula II as an antiarthritic or anti-inflammatory agent.

SUMMARY OF THE INVENTION

This invention provides a method of treating humans with an effective amount of a compound of Formula I or II, wherein

Formula I

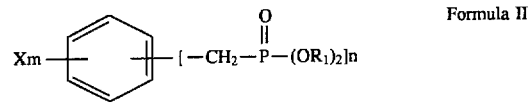

Formula II $R_1$ is independent and selected from the group consisting of hydrogen, $Na^+$, $K^+$, $NH_4^+$, $(R_2)_4N^+$, $C_1$–$C_{10}$ alkyl, —$CH_2C_6H_5$, or —$C_6H_5$ or adjacent $R_1$ can be taken together to form —$CH_2(CH_2)_pCH_2$— or —$CH_2C(CH_3)_2CH_2$— (where p is 0–2);

Ar is (a) 1- or 2-naphthyl, 2-, 3-, or 4-pyridinyl, 1-, 2-, or 9-anthryl, 1-, 2-, 3-, 4-, or 9-phenanthryl, 1-, 2-, or 4-pyrenyl, biphenyl, (b) phenyl substituted with 1 through 5 -F, (c) phenyl substituted with 1 through 3 —Cl, —Br, —$R_2$, or —$OR_2$, (d) phenyl substituted with —$CF_3$, —COOH, —$COOR_2$, —$OCOR_2$, —$SO_2NH_2$, —$SO_2NR_2$, —$N(R_2)_2$, —$NHSO_2R_2$, —$NHCOOR_2$, —CN, (e) naphthyl substituted with —F, —Cl, —Br, —I, —$R_2$, —$OR_2$, —OH, —$CF_3$, —COOH, —$COOR_2$, —$OCOR_2$, —$SO_2NH_2$, —$NHSO_2R_2$, or —$NHCOR_2$;

X is independently —OH or —Cl;

$R_2$ is $C_1$–$C_{18}$ alkyl;

n is 3 or 4; and m is 2 or 3;

as a treatment of arthritic disease and disease characterized by chronic inflammatory immunopathological mechanisms. The preferred phosphonates of Formula I are 4-dodecyloxy-benzylphosphonic acid dimethyl ester, (2-naphthalenylmethyl)phosphonic acid dimethyl ester, and ([1,1'-biphenyl]-2-ylmethyl)phosphonic acid dimethyl ester. The preferred phosphonates of Formula II are [1,3,5-benzenetriyltris-(methylene)]trisphosphonic acid, hexamethyl ester, [1,2,4-benzenetriyltris(methylene)]trisphosphonic acid, hexamethyl ester, and [1,2,4,5-phenylenetetrakis(methylene)]tetrakisphosphonic acid, octamethyl ester.

DETAILED DESCRIPTION

The invention relates to the use of the compounds of Formulas I and II, above, and their pharmacologically acceptable salts for the therapeutic treatment of human arthritic disease and disease characterized by chronic inflammatory immunopathological mechanisms. Included within these diseases are inflammatory, granulomatous, calcemic, atherosclerotic, and hypertensive disease. Particularly preferred utilities are for the treatment of inflammation and arthritis.

When used to treat humans in the method of the invention it is preferred that $R_1$ is an alkyl; methyl is preferred. The methyl phosphonate esters are preferred with the dimethyl esters being most preferred.

Administration of the compounds of Formula I or II following the method of the invention is in any amount effective to control or eliminate the pain, discomfort, or clinical symptoms for which treatment is sought. As a general rule, this is accomplished by the use of dosage amounts similar to known and commercially available anti-arthritic and anti-inflammatory products, e.g., phenylbutazone, indomethacin, gold sodium thiomulate, dexamethazone, penicillamine, sodoxicam, and naproxen. The preferred method of administration is orally at about 2 to 100 mg, administered 1–6 times a day. The preferred dose is between about 0.01 to 10 µg/kg/min when by intravenous infusion. The daily dose is about 0.01 to about 100 mg/kg body weight; the preferred daily dose is about 0.03–85 mg/kg. Administration may be accomplished by any number of means, including, but not limited to, oral, anal, buccal, intravenous, subcutaneous, intramuscular, topical, or aerosol. However, the means of administration and the specific dose for a patient depends on a wide variety of factors, for example on the efficacy of the specific compound employed (alone or when used in combination with other medicaments), the severity of the disorder for which therapy is sought, on the age, weight, health, sex, and diet of the patient, on the method of administration, and on the excretion rate. These factors are recognized by those skilled in the art. In addition, the adaptation of the formulation or the mode or amount of compound administered to accommodate these factors are well known in the art and require no special mention.

When used in a pharmaceutical composition of the invention it is possible to modify the compounds into forms suitable for administration as mentioned above. In any pharmaceutical formulation, at least one compound of Formula I and/or one of its pharmacologically acceptable salts are mixed or combined with at least one carrier or vehicle. Carriers or vehicles include inorganic or organic substances which are suitable for administration and which do not react with the new compounds. Examples of suitable carrier vehicles include water, vegetable oils, benzyl alcohols, polyethylene glycols, gelatine, carbohydrates such as lactose or starch, magnesium stearate, talc, and vaseline. In particular, tablets, coated tablets, capsules, syrups, liquids, drops, or suppositories are used for oral, anal, or buccal applications. When injection or parenteral is the route of administration, solutions of an oily or aqueous nature are preferred, but suspensions, emulsions, or implants may be used as well. Ointments, creams, or powders are used for topical administration, and any suitable aerosol form for inhalation therapy. It is also possible to sterilize and/or lyophilize these compounds for subsequent use in the preparation of products.

The formulations may also contain one or more pharmacologically acceptable auxiliaries, such as lubricants, preservatives, stabilizers, wetting agents, emulsifiers, salts, buffers, colorants, flavorings, and aromatic substances.

Terms used in this specification and claims have the following definitions:

The carbon atom content of the various hydrocarbon-containing moieties is indicated by designating the minimum and maximum number of carbon atoms in the moiety, i.e. $C_m$–$C_n$ indicates a moiety of integer "m" to the integer "n" carbon atoms, inclusive, and encompasses isomeric forms. For example, $C_1$–$C_6$ alkyl refers to an alkyl of one to six carbons, inclusive, including the isomeric forms.

Throughout the disclosure and claims, common shorthand chemical terms are used. For example:

Temperatures are in degrees Celsius.

The letter "h" means hours.

Units are measured in the metric system and its standard abbreviations are used.

The term "NMR ($CDCl_3$) δ" means proton nuclear magnetic resonance spectral analysis in delta scale units.

"IR" means infrared spectral analysis.

"UV" means ultraviolet spectral analysis.

"MS" means mass spectral analysis in mass to charge ratio.

"TLC" means thin layer chromatography.

Representative Compounds of Formula I

All starting materials are known and are commercially available, or are readily prepared from known or readily available starting materials. Bromomethyl, chloromethyl derivatives of benzene, naphthalene, biphenyl, and anthracene are available from Aldrich Chemical Company. In addition, compounds used in the method of the invention may be available from commercial vendors. For example, (benzyl)phosphonic acid diethyl ester is available from Aldrich Chemical Company. However, many of the compounds useful in the method of the invention are synthesized following the preparative techniques described below. These methods follow techniques which are known, or readily acquired, by one skilled in the art. Examples of such techniques are:

J. R. Wiseman et al., J. Org. Chem. (1980) 45, 516 and E. F. M. Stephenson, Organic Synthesis, Coil. Vol. IV, 984 (bromination of substituted xylenes);

L. Ernst, Org. Magnetic Resonance, (1977) 9, 35, and L. Ernst, J. C. S. Chem. Commun. (1977) 375 (spectroscopic properties of methylenephosphonates);

L. M. Nguyen et al., J. Med. Chem. (1987) 30, 1426 (hydrolysis/esterification); and J. Petrova et al., Synthesis, (1975) 658 and A. F. Kluge, Tetrahedron Letters, (1978) 39, 3629 (methylene alkylation).

The synthesis of compounds of the invention proceed, generally, as outlined below.

Methylcarboxylates may serve as starting materials. Proceeding from methylcarboxylate, the carboxylate is reduced first, to the corresponding hydroxymethyl and in a second step, to the bromide or chloride. Generally, however, it is preferred to obtain the bromides from commercial vendors. In the presence of an organic solvent, the bromide or chloride is reacted with excess trialkyl phosphite to provide the phosphonate ester. These products are useful in the method of the invention or may be further modified as described below. These reactions are carried out under ambient to reflux temperature conditions, e.g. 25 to 130 degrees, for a time sufficient to effect as complete a reaction as possible, e.g. from 3 to 48 hours.

The ester groups of the phosphonate may be hydrolyzed by any volatile mineral acid to the di-acid, e.g., hydrochloric or hydrobromic, or the ester groups may be selectively removed with bromotrimethyl silane to provide a monoacid. Esterification of the diacid, and, similarly the monoacid, with a second ester group is achieved conveniently with an orthacid or diazoalkane; the diazoalkane, e.g. diazomethane, is believed to be most useful in esterification of sterically hindered acids.

The α-hydroxy and α-chlorophosphonates are synthesized following procedures known in the art. Briefly, the α-hydroxyphosphonates are produced by reacting the dialkyl phosphite and the desired aldehydes (Ar—CHO) to produce the α-hydroxy phosphonate. Alternatively, the dialkyl phosphite can be converted by trimethylsilylchloride to the trimethylsilyl dialkylphosphite. The trimethylsilyl dialkylphosphite is then conveniently reacted with the desired aldehyde (Ar—CHO), which, after hydrolysis of the trimethylsilyl group, results in the α-hydroxy phosphonate. The α-chlorophosphonates compounds of the invention can be conveniently produced by reacting thionylchloride with the corresponding α-hydroxy species.

The substituted aryls of the invention are produced using corresponding bromomethylenes or chloromethylenes as starting materials using synthetic techniques as described above or, alternatively, from commercial sources. The esterification and alkylation of these compounds is also accomplished following the above procedure.

As each step of the synthesis is completed, the reaction mixture can be treated by conventional chemical processing procedures, e.g., by dilution, solvent partitioning, filtration, concentration, and cooling, to separate the products from the reactants and solvents. The solid compounds of the invention have melting points generally in the range of about 50 to greater than 250 degrees, and thus are easily separated by filtration or centrifugation; oils or liquids are separated by chromatographic methods. Solids may be obtained in purer form by recrystallization from hot organic solvents; solids, liquids, and oils are further purified by chromatographic methods or distillation.

The conditions described here and in the examples that follow for the synthesis and purification of the compounds of the invention may be altered depending on the choice of reactants and solvents, the batch size, the degree to which the reaction is to be carried to completion, and other factors of concern to the chemist. Such modifications and alterations are known by those skilled in the art and require no special mention.

By following the preceding description, and without further elaboration, one skilled in the art can utilize the present invention to the fullest extent. The representative examples and demonstrations of utility that follow are merely illustrative, and not limiting, of the disclosure.

Preparation 1 4-Dodecyloxybenzyl alcohol

A solution of 4-dodecyloxybenzoic acid (10.77 g, 0.035M) in dry THF (100 mL) is added dropwise over a period of 10 min to a stirred mixture of lithium aluminum hydride (1.4 g, 0.037M) and THF (50 mL). The mixture is allowed to stir for 24 hr at room temperature and then is quenched by careful addition of a THF-water (3: 1) mixture while cooling the system in an ice-water bath. The mixture is then acidified with aq. 2N HCl to dissolve aluminum salts and extracted with ether (3×). The ether extracts are combined, dried ($Na_2SO_4$), filtered, and concentrated to give a white solid (10.14 g). The solid is recrystallized from hexane to give colorless, shiny crystals of the title compound (9.13 g, 89%), mp 66.5°–67° C.

Preparation 2 4-Dodecyloxybenzyl chloride

A solution of 4-dodecyloxybenzyl alcohol (Preparation 1, 2.92 g, 0.0010M) in benzene (40 mL) is added dropwise to a stirred solution of thionyl chloride (3.0 mL, 4.97 g, 0.04M) over a period of 20 minutes. The solution is stirred at room temperature for 0.5 hr and then is heated at reflux temperature for 3 hours (monitoring of the reaction by TLC may be deceptive since the product is hydrolyzed to starting alcohol when placed on a silica gel plate; the plate must be developed immediately after the sample is applied). Benzene and excess thionyl chloride are removed under reduced pressure. The crude product is used in Example 1 without further purification.

Compound 1 4-Dodecyloxybenzylphosphonic acid, dimethyl ester

A solution of the crude chloride (Preparation 2, 0.012M) in trimethylphosphite (10 mL, 10.5 g, 0.085M) is heated at the reflux temperature under a nitrogen atmosphere for 48 hours, after which a trace of starting chloride is detected by TLC. Excess trimethylphosphite is removed under reduced pressure, giving a colorless oil. The oil is chromatographed over silica gel (40–63 mμ, 400 g, 45 mL fractions) using ethyl acetate for application and elution. Fractions 47–74 are pooled and concentrated (3.16 g). An NMR spectrum indicated the presence of a small impurity (doublet at δ 3.76) which is removed by placing the oil under vacuum for 24 hours. The product crystallized, mp 30°–31° C.

IR (mull) 1614, 1584, 1515, 1298, 1247, 1189, 1181, 1054, 1045, 1038, 861,842, 834, 828, 814, 731 $cm^{-1}$. $^1H$ NMR ($CDCl_3$) δ 7.19 (m, 2H, aromatic), 6.84 (m, 2H, aromatic), 3.93 (t, 2H, J=6.6 Hz, —$CH_2OAr$), 3.66 (d, 6H, J=10.7 Hz, —$OCH_3$), 3.10 (d, 2H, J=21.1 Hz, —$CH_2P$), 1.77 (m, 2H, —$CH_2$—), 1.51–1.16 (m, 18H, —$CH_2$—), 0.88 (t, 3H, J=6.5 Hz, —$CH_3$). MS 384, 216, 107. Anal. Calc'd for $C_{21}H_{37}O_4P$: C, 65.60; H, 9.70; P, 8.06. Found: C, 65.44; H, 9.57; P, 8.10.

Compound 2 (2-Methyl-1-naphthalenylmethyl)phosphonic acid, dimethyl ester

A solution of 1-chloromethyl-2-methylnaphthalene (9.50 g, 0.050M) in trimethylphosphite (15 mL, 15.8 g, 0.13 M) is heated at reflux temperature for 48 hours. Excess trimethylphosphite is removed under reduced pressure, giving a yellow oil which is chromatographed over silica gel (40–63 μ, 400 g, 50 mL fractions) using ethyl acetate for elution of the column. Fractions 18-21 are pooled and after concentration gave a white solid (7.78 g). Recrystallization from ether-pentane gave title compound (6.94 g) as colorless crystals, mp 54°–57° C.

IR (mull) 1249, 1182, 1177, 1069, 1056, 1028, 922, 843, 804, 794, 784, 747 cm$^{-1}$. $^1$H NMR (CDCl$_3$) δ 8.08 (d, 1H, aromatic H), 7.80 (d 1H, aromatic H), 7.69 (m, 1H, aromatic H), 7.53 (t, 1H, aromatic H), 7.43 (t, 1H, aromatic H), 7.33 (d, 1H, aromatic H), 3.70 (d, 2H, J=22 Hz, —CH$_2$—), 3.55 (d, 6H, J=10.7 Hz, —OCH$_3$), 2.60 (m, 3H, —CH$_3$). MS C$_{14}$H$_{17}$O$_3$P requires 264.0915, found: 264.915, 155, 141, 128, 115. Anal. Calc'd for C$_{14}$H$_{17}$O$_3$P: C, 63.63; H, 6.49; P, 11.72. Found: C, 63.58; H, 6.55; P, 11.97.

Compound 3 (1-Naphthalenylmethyl)phosphonic acid dimethyl ester

A solution of 1-bromomethylnaphthalene (5.0 g of 98% material, 0.022M) in toluene (50 mL) is heated at reflux in a flask equipped with a Dean-Stark trap to dry the starting material and the toluene (N$_2$ atmosphere). After the solution is refluxed for one hour and 25 mL of toluene is removed via the Dean-Stark trap, the reaction mixture is treated with trimethylphosphite (10 mL, 0.085 M). The mixture is heated to reflux temperature for 24 hours. The toluene and the excess trimethylphosphite are removed at a reduced pressure to yield an oil. The oil is chromatographed over silica gel (400 g, 40–63 μm, EtOAc, 50 mL fractions) using EtOAc to elute the column. Fractions 10-20 contained (5.49 g, 0.0219M, 99%) of the title compound as a viscous liquid.

IR (liquid film) 2954, 1597, 1511, 1463, 1397, 1272, 1255, 1215, 1183, 1057, 1029, 1013, 881, 864, 854, 832, 805, 722, 639 cm$^{-1}$. $^1$H NMR (CDCl$_3$): δ 5 8.08, 7.85, 7.78 (3m, 3H, aromatic), 7.49 (m, 4H, aromatic), 3.65 (d, 2H, J=22.1 Hz, —CH$_2$P—), 3.59 (d, 6H, J=10.8 Hz, —OCH$_3$). MS: C$_{13}$H$_{15}$O$_3$P requires 250.0759, found: 250.0756, 141, 115 m/e. Anal. calc'd for C$_{13}$H$_{15}$O$_3$P: C, 62.40; H, 6.04; P, 12.38. Found: C, 61.68; H, 6.25; P, 12.17.

Compound 4 (2-Naphthalenylmethyl)phosphonic acid dimethyl ester

A solution of 2-bromomethylnaphthalene (4.42 g, 0.020M) and trimethylphosphite (5 mL, 5.26 g, 0.042M) in dry toluene (100 mL) is heated at reflux temperature for 120 hours The reaction is incomplete, so the volume of the solution is reduced to 25 mL, additional trimethylphosphite (5 mL) is added, and the solution heated to reflux for another 24 hours. Solvent is removed under reduced pressure and the solid white residue is chromatographed over silica gel (40–63 μm, 195 g, ethyl acetate). Elution of the column with ethyl acetate gave title compound (4.63 g) as a white solid which after crystallization from ether-hexane had mp 80°–81° C.

IR (mull): 1245, 1049, 1030, 831, 752 cm$^{-1}$. $^1$H NMR (CDCl$_3$): δ 7.80, 7.45 (2m, 7H, aromatic), 3.68 (d, 6H, J=10.7 Hz, —OCH$_3$), 3.34 (d, 2H, J=21.7 Hz, —CH$_2$P—). MS: C$_{13}$H$_{15}$O$_3$P requires 250.0759. Found: 250.0760, 218, 154, 141, 115 m/e. Anal. calc'd for C$_{13}$H$_{15}$O$_3$P: C, 62.40; H, 6.04; P, 12.38. Found: C, 62.39; H, 5.89; P, 12.44.

Compound 5 (2-Naphthalenylmethyl)phosphonic acid

A solution of (2-naphthalenylmethyl)phosphonic acid dimethyl ester (Compound 4, 520 mg, 2.08 mM) in concentrated hydrochloric acid (15 mL) is heated at reflux temperature for ten hours. The reaction mixture is then cooled and allowed to stand at room temperature until a white precipitate is formed. The reaction is cooled to room temperature and the aqueous HCl is removed at a reduced pressure. The white solid residue is recrystallized from water to give 0.206 g of the title compound as white crystals, mp 234°–236° C. with softening at 225° C.

IR (mull): 3050, 3019, 1283, 1273, 1250, 1224, 1208, 1059, 1002, 967, 958, 952, 947, 931, 861,828, 753, 745, 643 cm$^{-1}$. $^1$H NMR (CD$_3$OD): δ 7.79–7.44 (m, 7H, aromatic), 3.27 (d, 2H, J–20 Hz, —CH$_2$P). MS: C$_{11}$H$_{11}$O$_3$P requires 222.0446, found: 222.0457, 141,115 m/e. Anal. calc'd for C$_{11}$H$_{11}$O$_3$P: C, 59.47; H, 4.99; P, 13.94. Found: C, 59.13; H, 4.96; P, 14.01.

Compound 6 ([1,1'-Biphenyl]-2-ylmethyl)phosphonic acid dimethyl ester

A solution of 2-(bromomethyl)biphenyl (4.94 g, 0.020M) and trimethylphosphite (5.0 mL, 5.26 g, 0.042M) in toluene (25 mL) is heated at reflux temperature for 24 hours Toluene and excess trimethylphosphite are removed under reduced pressure and the oily residue is chromatographed over silica gel (195 g, 40–63 μm, EtOAc, 50 mL fractions) using EtOAc to elute the column. The title compound (5.35 g, 0.0194M, 97%) is obtained in fractions 10–19 and is a colorless viscous oil.

IR (liquid film): 2952, 1481, 1451, 1438, 1253, 1228, 1185, 1058, 1051, 1031, 1010, 856, 837, 816, 793, 779, 759, 747, 705, 617 cm$^{-1}$. $^1$H NMR (CDCl$_3$): δ7.36 (m, 9H, aromatic), 3.57 (d, 6H, J=10.7 Hz, —OCH$_3$), 3.21 (d, 2H, J=22.2 Hz, —CH$_2$P—). MS: 276 (M$^+$), 244, 167, 166, 152 m/e. Anal. calc'd for C$_5$H$_{17}$O$_3$P: C, 65.21; H, 6.20; P, 11.21. Found: C, 64.62; H, 6.37; P, 11.26.

Compound 7 ( [1,1'-B phenyl]-2-ylmethyl)phosphonic acid monosodium salt, monomethyl ester A solution of ([1,1'-Biphenyl]-2-ylmethyl)phosphonic acid dimethyl ester (Compound 6, 537 mg, 2.07 mM) in methyl ethyl ketone (5 mL) is treated with sodium iodide (313 mg, 2.07 mM) and heated at reflux temperature for six hours. A white precipitate had formed. The methyl ethyl ketone is removed at a reduced pressure. The white residue is recrystallized from water to give 433 mg of title compound as white solid.

IR (mull): 3499, 3381, 1480, 1436, 1201, 1186, 1147, 1072, 1057, 1049, 1031, 817, 793, 762, 752, 747, 730, 707 cm$^{-1}$. $^1$H NMR (CD$_3$OD): δ 7.69–7.12 (m, 9H, aromatic), 3.32 (d, 3H, —OCH$_3$), 2.99 (d, 2H, J=21.1 Hz, —CH$_2$P—). Anal. calc'd for C$_{14}$H$_{14}$O$_3$: C, 59.16; H, 4.97; P, 10.90. Found: C, 58.67; H, 5.46; P, 10.69.

Compound 8 ([1,1'-Biphenyl]-2-ylmethyl)phosphonic acid

A solution of ([1,1'-Biphenyl]-2-ylmethyl)phosphonic acid dimethyl ester (Compound 6, 515 mg, 1.87 mM) in concentrated hydrochloric acid (5 mL) is heated at reflux temperature for six hours. The reaction is then allowed to stand at room temperature until a white precipitate is formed. The aqueous HCl is removed under reduced pressure. The white solid is recrystallized from water to yield 300 mg of title compound as white crystals, mp 168.5°–169° C.

IR (mull): 3085, 3060, 3028, 2798, 2370, 2258, 2139, 1481, 1451, 1434, 1401, 1256, 1190, 1170, 1146, 1108 cm$^{-1}$. $^1$H NMR (CD$_3$OD): δ 7.59–7.19 (m, 9H, aromatic), 3.10 (d, 2H, J=22.1 Hz, —CH$_2$P—). MS: C$_{13}$H$_{13}$O$_3$P requires 249.0681. Found: 249.0678. Anal. calc'd for C$_{13}$H$_{13}$O$_3$P: C, 62.91; H, 5.28; P, 12.48. Found: C, 62.51; H, 5.27; P, 13.14.

Compound 9 ([1,1'-Biphenyl]-4-ylmethyl)phosphonic acid dimethyl ester

A solution of 4-(chloromethyl)biphenyl (4.12 g, 0.020M) in trimethylphosphate (10 mL, 10.5 g, 0.085M) is heated at reflux temperature for 60 hours. The excess trimethylphosphite is removed under reduced pressure and the solid residue is chromatographed (400 g of 40–63 μm silica gel, 50 mL fractions). The sample is applied to the column in a minimum amount of EtOAc and the column is eluted with 50% EtOAc-hexane (1.2 L), 75% EtOAc-hexane (2 L), and with EtOAc. Fractions 88–136 contained the dimethyl ester (4.98 g, 0.0180M, 90%) which is crystallized from ether-pentane to give 4.09 g of title compound as white crystals, mp 70°–71° C.(fused), 76.5°–77.5° C.

IR (mull): 1485, 1256, 1049, 1022, 1009, 868, 835, 809, 796, 770, 737, 702, 639 cm$^{-1}$. $^1$H NMR (CDCl$_3$): δ 7.57 (m, 4H, aromatic), 7.39 (m, 5H, aromatic), 3.70 (d, 6H, J=10.8 Hz, —OCH$_3$), 3.21 (d, 2H, J=21.7 Hz, —CH$_2$P—). MS: C$_{15}$H$_{17}$O$_3$P requires 276.0915. Found: 276.0919, 167 m/e. Anal. calc'd for C$_{15}$H$_{17}$O$_3$P: C, 65.21; H, 6.20; P, 11.21. Found: C, 65.31; H, 6.43; P, 14.92.

Compound 10 (9-Anthracenylmethyl)phosphonic acid dimethyl ester

A solution of 9-(chloromethyl)anthracene (2.5 g, 0.011M) in trimethylphosphite (5 mL, 5.26 g, 0.042 M) is heated at reflux temperature for 72 hours. Excess trimethylphosphite is removed under reduced pressure and the residue is chromatographed over silica gel (400 g, 40–63 μm, CH$_2$Cl$_2$, 50 mL fractions) using CH$_2$Cl$_2$ (60 fractions) and 2% CH$_3$OH in CH$_2$Cl$_2$ for the remaining fractions. Fractions 86–93 (2.99 g) are found to contain desired material and an impurity and are rechromatographed (400 g silica gel, 40–63 lam, CH$_2$Cl$_2$, 50 mL fractions) using 2.5% acetone-CH$_2$Cl$_2$ to elute the column. Fractions 100–160 contains compound (1.495 g, 0.00498M, 45%) as a yellow solid. Crystallization from ethyl acetate gives the title compound (1.34 g) as yellow needles, mp 152°–153° C.

IR (mull): 1450, 1252, 1229, 1178, 1057, 1036, 1024, 885, 828, 798, 792, 738, 731, 631, 601 cm$^{-1}$. $^1$H NMR (CDCl$_3$): δ 8.08, 7.85, 7.78 (3 m, 3H, aromatic), 7.49 (m, 4H, aromatic), 3.65 (d, 2H, J=22.1 Hz, —CH$_2$P—), 3.59 (d, 6H, J=10.8 Hz, —OCH$_3$). MS: 300 (M$^+$), 191 m/e. Anal. calc'd for C$_{17}$H$_{17}$O$_3$P: C, 68.00; H, 5.71; P, 10.32. Found: C, 68.03; H, 5.82.

Compound 11 4-Fluorobenzylphosphonic acid, dimethyl ester

A mixture of 4-fluorobenzyl bromide (4.86 g, 0.026M) and trimethylphosphite (10 mL, 0.085M) is heated at the reflux temperature for 48 hours. The solution is cooled and excess trimethylphosphite is removed under reduced pressure. The crude product is chromatographed over silica gel (40–63 mμ, 400 g, 45 mL fractions, ethyl acetate), eluting with ethyl acetate. Fractions 41–80 are combined, concentrated, and placed under vacuum for 36 hours. The product (4.52 g) is a colorless oil.

IR (liquid film): 2956, 1511, 1250, 1226, 1190, 1185, 1160, 1059, 1057, 1032, 865, 810 cm$^{-1}$. $^1$H NMR (CDCl$_3$): δ 7.27 (m, 2H, aromatic), 7.01 (t, 2H, J=8.9 Hz, aromatic), 3.67 (d, 6H, J=13.8 Hz, —OCH$_3$), 3.14 (d, 2H, J=21.4 Hz, —CH$_2$—). MS: 218 (M+), 203, 122, 109. Anal. calc'd for C$_9$H$_{12}$FO$_3$P: C, 49.55; H, 5.55; P, 14.20. Found: C, 49.48; H, 5.67; P, 14.26

Compounds 12–18

The following compounds are prepared by reacting a (bromomethyl)aryl (synthesized, where appropriate, following a procedure suitably adapted from Preparations 1 and 2), with a trialkylphosphite as described in the Compounds. Those skilled in the art recognize that necessary and appropriate adjustments may be required in reaction ratios and conditions and/or chromatography conditions in order to obtain the title compound. Such modifications are well known and within the ability of the skilled artisan.

Compound 12 2-Methylbenzylphosphonic acid, dimethyl ester

Following the procedure of Compound 11, 2-methylbenzyl bromide is reacted with trimethylphosphite.

Compound 13 3-Methylbenzylphosphonic acid, dimethyl ester

Following the procedure of Compound 11, 3-methylbenzyl bromide is reacted with trimethylphosphite.

Compound 14 4-Methylbenzylphosphonic acid, dimethyl ester

Following the procedure of Compound 11, 4-methylbenzyl bromide is reacted with trimethylphosphite.

Compound 15 2-Fluorobenzylphosphonic acid, dimethyl ester

Following the procedure of Compound 11, 2-fluorobenzyl bromide is reacted with trimethylphosphite.

Compound 16 3-Fluorobenzylphosphonic acid, dimethyl ester

Following the procedure of Compound 11, 3-fluorobenzyl bromide is reacted with trimethylphosphite.

Compound 17 2-Chlorobenzylphosphonic acid, dimethyl ester

Following the procedure of Compound 11, 2-chlorobenzyl bromide is reacted with trimethylphosphite.

Compound 18 (4-Chloro-1-napthaleneylmethyl)phosphonic acid, dimethyl ester

Following the procedure of Compound 11, 4-chloro-1-bromomethylnaphthalene is reacted with trimethylphosphite.

Compound 19 (α-Hydroxybenzyl)phosphonic acid, diethyl ester

A solution of trimethylsilylchloride (16.4 g, 0.151M) and diethyl phosphite (14.0 g, 0.101M) in diethyl ether (100 mL) is treated with triethylamine (15.3 g, 0.151M) at room temperature and under a stream of nitrogen. The reaction mixture becomes milky instantly. The mixture is heated to reflux for 16 hours, where it is gradually allowed to cool to room temperature. Pentane (100 mL) is added followed by filtration using a Buchner funnel. The solution is concentrated in vacuo and the crude is distilled using a micro-distillation apparatus to obtain, after a forerun, 14.98 g (0.071M, 71%) of trimethylsilyldiethylphosphite as a clear oil: bp 70°–70.5° C./20 mm (lit REF reports a bp of 76°–77° C./20 mm).

Benzaldehyde (1.73 g, 0.0163M) and the trimethylsilyldiethylphosphite (3.34 g, 0.016M) are combined in a sealed tube. The mixture is heated to 110° for 3 hours and it is allowed to stand at room temperature overnight. The mixture is treated with a trifluoro acetic acid solution in methanol (10$^{-3}$M, 50 mL) and allowed to stir overnight at room temperature. Volatile are removed in vacuo to obtain 3.56 g of a white solid (0.014M, 91%). A portion of this solid (1.0 g) is crystallized from hexane to obtain (α-hydroxybenzyl)phosphonic acid diethyl ester as colorless needles (0.91 g): mp 83°–83.5° C. (lit REF reports amp of 83.0°–83.2° C).

Compound 20 (m-Fluoro-α-hydroxybenzyl)phosphonic acid, diethyl ester

The procedure described for the preparation of Compound 19 is used except that 3-fluorobenzaldehyde (1.49 g, 0.012M) is used in place of benzaldehyde. The solid obtained is recrystallized from hexane to obtain 2.474 g (0.009 M, 79%) of colorless short needles: mp 81°–82° C.

$^1$H NMR (CDCL$_3$/TMS): δ 7.36–7.23 (m, 3H, Ar—H), 7.03–6.97 (m, 1H, Ar—H), 5.04 (d, J=12 Hz, 1H, CH—OH), 4.50 (br s, 1H, OH), 4.14–3.97 (m, 4H, CH$_2$CH$_3$), 1.29 (t, J=7 Hz, 6H, CH$_3$) 1.25 (t, J=7 Hz, 6H, CH$_3$); $^{13}$C NMR (CDCl$_3$): δ 162.5 (d, J=248 Hz, CF), 139.0 (d, J=5 Hz, Ph), 129.6 (d, J=8 Hz, Ph) 122.4 (d, J=9 Hz, Ph), 114.7 (d, J=21 Hz, Ph), 113.9 (d, J=28 Hz, Ph), 70.2 (d, J$_{CP}$=158 Hz, C—P), 63.4 (d, J$_{COP}$=7 Hz, CH$_2$OP(O)), 63.1 (d, J$_{COP}$=7 Hz, CH$_2$OP(O)), 16.2 (d, J$_{CCOP}$=6 Hz, CH$_3$CH$_2$OP(O)); $^{31}$P NMR (CDCl$_3$): δ 19.41; mass spectrum 262.0784 (C$_{11}$H$_{16}$FO$_4$P requires 262.0770). Anal. calc'd. for C$_{11}$H$_{16}$FO$_4$P: C, 50.38; H, 6.15; P, 11.81. Found: C, 50.44; H, 6.20; P, 12.04.

Compound 21 (α-Hydroxybenzyl-3-pyridinylmethyl)phosphonic acid, diethyl ester

The procedure described for the preparation of Compound 19 is used except that 3-pyridinecarboxaldehyde (1.419 g, 0.0133M) is used in place of benzaldehyde. The crude product after the desilylation is chromatographed over flash silica gel (230 g, 0.042–0.063 mm, 4 cm width) and eluted with 8% CH$_3$OH/CH$_2$Cl$_2$ to obtain 11 fractions of 150 mL each. Fractions 5–10 contain 2.088 g (64%) of (α-hydroxybenzyl-3-pyridinylmethyl)phosphonic acid diethyl ester as a pale oil. The oil solidifies upon standing at 4°–5° C. overnight and is crystallized (0.768 g) from ethyl acetate/hexane to obtain 0.672 g of colorless needles: mp 238° C.

$^1$H NMR (CDCl$_3$/TMS): δ 8.63 (s, 1H, Ar—H), 8.49 (d, J=6 Hz, 1H, Ar), 7.90 (dd, J=2, 8 Hz 1H, Ar—H), 7.30 (dd, J=5, 7 Hz, 1H, Ar—H), 5.08 ( d, J=12 Hz, 1H, ARCH), 4.16–4.02 (m, 4H, CH$_2$CH$_3$), 1.29–1.22 (m, 6H, CH$_2$CH$_3$); $^{13}$C NMR (CDCl$_3$): δ 148.6 (Ar), 148.1 (d, J=6 Hz, Ar), 134.8 (Ar), 133.2 (Ar), 123.0 (d, J=2 Hz, Ar), 68.2 (d, J=162 Hz, ARCH), 63.2 (d, J=7 Hz, CH$_2$OP(O)), 62.9 (d, J=7 Hz, CH$_2$OP(O)), 16.2 (CH$_3$), 16.1 (CH$_3$); $^{31}$P NMR: δ 19.19. Anal. calc'd. for C$_{10}$H$_{16}$O$_4$NP: C, 48.98; H, 6.58; N, 5.71; P, 12.63. Found: C, 48.86; H, 6.55; P, 12.86.

Compound 22 (α-Hydroxy-2-naphthylmethyl)phosphonic acid, diethyl ester

2-Naphthaldehyde (1.67 g, 0.0107M) is mixed with diethyl phosphite (2.14 g, 0.0156M) under a nitrogen atmosphere and heated to 130°–135° C. for 3 hours. The mixture is diluted with methylene chloride and water and layers are separated. The aqueous layer is extracted with methylene chloride (2 times). The combined organic layers are dried (MgSO$_4$), filtered and concentrated in vacuo to obtain 3.835 g of crude material. The crude is chromatographed over flash silica gel (210 g, 0.042–0.063 mm, 4 cm width) and eluted with 1–2% CH$_3$OH/CH$_2$Cl$_2$ to obtain 169 fractions of 25 mL each. Fractions 104–165 contain 1.85 g (59%) of the desired product as a white solid. The solid is crystallized from hexane/ethyl acetate to obtain a first crop of (α-hydroxy-2-naphthylmethyl)phosphonic acid diethyl ester as colorless short needles (1.091 g): mp 90.1°–91.3° C.

$^1$H NMR (CDCl$_3$/TMS): δ 7.95 (s, 1H, At), 7.84–7.80 (m, 3H, At), 7.61–7.58 (m, 1H, Ar), 7.50–7.44 (m, 2H, At), 5.20 (d, J=11 Hz, 1H, ARCH), 4.12–3.94 (m, 4H, CH$_2$OP(O)), 1.25 (t, J=7 Hz, CH$_3$), 1.20 (t, J=7 Hz, CH$_3$); $^{13}$C NMR (CDCl$_3$): δ 133.8, 132.8, 127.8, 127.6, 127.4, 125.8, 124.7, 124.6, 70.6 (d, J=158 Hz, ArCH), 63.1 (d, J=7 Hz, CH$_2$OP(O)), 62.9 (d, J=7 Hz, CH$_2$OP(O)), 16.1 (CH$_3$), 16.0 (CH$_3$); $^{31}$P NMR (CDCl$_3$): δ 21.90. Anal. calc'd. for C$_{15}$H$_{19}$O$_4$P: C, 61.22; H, 6.51; P, 10.53. Found: C, 61.14; H, 6.47; P, 10.71.

Compound 23 [m-(Trifluoromethyl)-α-hydroxybenzyl]phosphonic acid, diethyl ester

The procedure described for the preparation of Compound 22 is used except that α,α,α-trifluorotolualdehyde (2.52 g, 0.0145M) is used in place of 2-naphthaldehyde. The crude is chromatographed over flash silica gel (500 g, 0.042–0.063 mm, 5 cm width) and eluted with 2% CH$_3$OH/CH$_2$Cl$_2$ to obtain 100 fractions of 20 mL each. Fractions 51–75 contain 4.031 g (0.0130M, 89%) of the title compound as a clear oil.

$^1$H NMR (CDCl$_3$/TMS): δ 5 7.83 (s, 1H, ArH), 7.72 (d, J=8 Hz, 1H, ArH), 7.61 (d, J=8 Hz, 1H, ArH), 7.52 (t, J=8 Hz, 1H, ArH), 5.15 (d, J=11 Hz, 1H, CHOH), 4.19–4.06 (m, 4H, CH$_2$), 1.40–1.26 (m, 6H, CH$_3$); $^{13}$C NMR (CDCl$_3$): δ 137.9, 130.5 (q, J=32 Hz, ArC—CF$_3$), 130.3, 130.2, 124.6, 124.1 (q, J=271 Hz, CF$_3$), 70.1 (d, J=159 Hz, CHOH), 63.8 (d, J=7 Hz, CH$_2$), 63.3 (d, J=7 Hz, CH$_2$), 16.3, 16.2; $^{31}$P NMR (CDCl$_3$): δ 20.98. Anal. calc'd. for C$_{12}$H$_{16}$O$_4$F$_3$P: C, 46.16; H, 5.17; P, 9.92. Found: C, 46.02; H, 5.22; P, 10.18

Compound 24 (α-Hydroxy-1-naphthylmethyl)phosphonic acid diethyl ester

The procedure described for the preparation of Compound 22 is used except 1-naphthaldehyde (7.13 g, 0.0456M) is used in place of 2-naphthaldehyde. The crude is crystallized from a mixture of ethyl acetate and hexane to obtain 4.58 g (0.0156M, 34%) of the desired product as white crystals. A second recrystallization gives a first crop of (α-hydroxy-1-naphthylmethyl)phosphonic acid diethyl ester as fluffy needles (2.59 g): mp 119.8°–120.8° C. A second crop is also obtained (0.566 g): mp 119.9°–120.9° C.

$^1$H NMR (CDCl$_3$/TMS): δ 8.09 (d, J=8 Hz, ArH), 7.88–7.82 (m, 3H, ArH), 7.55–7.47 (m, 3H ArH), 5.8 (dd, J=5, 11 Hz, with D$_2$O: d, J=11 Hz, 1H, CHOH), 4.08–3.92 (m, 3H, CH$_2$), 3.81–3.73 (m, 1H, CH$_2$), 3.52 (dd, J=5, 11 Hz, with D$_2$O: bq, 1H, OH), 1.24 (t, J=7 Hz, CH$_3$); 1.05 (t, J=7 Hz, CH$_3$); $^{13}$C NMR (CDCl$_3$): δ 133.5, 132.9, 130.8 (d, J=6 Hz, ArCCHOH), 128.7, 125.9, 125.6, 125.5, 125.4, 125.3, 123.7, 67.1 (d, J=160 Hz, CHOH), 63.4 (d, J=7 Hz, CH$_2$), 63.0 (d, J=7 Hz, CH$_2$), 16.3–16.1 (m, CH$_3$); $^{31}$P NMR (CDCl$_3$): δ 22.30. Anal. calc'd. for C$_{15}$H$_{19}$O$_4$P: C, 61.22; H, 6.51; P, 10.52. Found: C, 61.21; H, 6.68; P, 10.67.

Compound 25 (α-Chlorobenzyl)phosphonic acid, diethyl ester

A solution of Compound 19 (1.00 g, 0.0041M) in thionyl chloride (1.63 g, 0.014M) is allowed to stir at room temperature for 16 hours. The thionyl chloride is removed in vacuo and the crude is poured over ice-water. The aqueous is extracted with ether (2 times). The ether layer is washed with sodium bicarbonate (saturated solution) (2 times) and water. The organic layer is dried (Na$_2$SO$_4$), filtered and concentrated to obtain 0.712 g of a clear oil. The crude is chromatographed over flash silica gel (0.040–063 mm, 100 g) and eluted with 1% acetone/CH$_2$Cl$_2$ to obtain 0.516 g (0.0020M, 48%) of the title compound as a clear oil. $^1$H NMR (CDCl$_3$/TMS): δ 7.56–7.52 (m, 2H, Ar), 4.40 –7.32 (m, 3H, ArH), 4.90 (d, J=14 Hz, 1H, CHCl), 4.23–4.12 (m, 2H, CH$_2$), 4.10–4.00 (m, 1H, CH$_2$), 3.95–3.84 (m, 1H, CH$_2$), 1.32 (dt, J=7.0, 0.6 Hz, 3H, CH$_3$), 1.17 (dt, J=7.0, 0.6 Hz, 3H, CH$_3$); $^{13}$C NMR (CDCl$_3$): δ 134.16 (d, J=3.0 Hz, Ar), 129.01–128.55 (m, Ar), 64.13–63.86 (m, CH$_2$), 53.67 (d, J=53.7 Hz, CHCl), 16.45–16.19 (m, CH$_3$); $^{31}$P NMR (CDCl$_3$): δ 17.82. Anal. calc'd. for C$_{11}$H$_{16}$O$_3$ClP: C, 50.30; H, 6.14; P, 11.79. Found: C, 50.06; H, 6.24; P, 11.66.

Biological Activity

The utility of the compounds of Formula I as a treatment for inflammatory disease is demonstrated by suppression of delayed-type hypersensitivity granuloma (DTH GRA) in mice. This assay is known by those skilled in the art as predictive of utility for the treatment of inflammatory conditions. This model measures the chronic aspects of immune-mediated inflammatory disease, such as the formation of inflammatory tissue resulting from cell proliferation (e.g., monocyte, macrophage, endothelium, fibroblast, lymphocyte) which is characteristic of, for instance, rheumatoid arthritis.

The procedure is described in detail in C. J. Dunn et al., 4th International Conference on the Therapeutic Control of Inflammatory Disease, 1988. Briefly, female CF-1 mice, 25 to 30 g, are obtained from The Upjohn Company breeding facility. DTH GRA lesions are induced in mBSA (bovine serum albumin) sensitized mice using mBSA-soaked 6 mm hydroxyapatite discs (Millipore Corp., Bedford, Mass.). The disc is implanted subcutaneously. The lesions are excised on Day 5. Wet weight (tissue and edema fluid) and dry weight (tissue) are determined for each lesion. The compounds are administered orally. When administered orally, the compound is dispersed in physiological sodium chloride solution at the time of DTH GRA induction (Day 1) and daily thereafter (Days 2, 3, and 4). Mice are sacrificed 24 hours after the last dose (Day 5). Administration is daily as outlined above. Untreated controls receive vehicle only.

Assay results are shown in Table 1. All of the tested compounds suppress DTH-induced granulomas. For instance, when administered orally at 10 mg/kg, 4-dodecyloxybenzylphosphonic acid, dimethyl ester (Compound 1), suppresses granulomas by 49 to greater than 51% (on a wet weight basis) and by 51 to 56% (on a dry weight basis). At doses as low as 1 mg/kg, Compound 4 ((2-naphthalenylmethyl)phosphonic acid dimethyl ester) suppresses granulomas by 54% (wet weight) and more than 50% (dry weight). Higher oral doses of Compound 4, up to 10 mg/kg, show suppression of between 40 and 67% (wet) and 47 and 57% (dry).

TABLE 1

DTH GRANULOMA ASSAY

| Compound #/ Compound Name | Dose (mg/kg) | % Change from Control (Wet Weight) | % Change from Control (Dry Weight) |
|---|---|---|---|
| 6 | 10.0 | −46.360 | −52.542 |
|  | 0.1 | −18.934 | 3.963 |
|  | 1.0 | −55.400 | −39.469 |
|  | 10.0 | −56.190 | −47.612 |
| 4 | 10.0 | −39.595 | −46.784 |
|  | 0.1 | −16.657 | −17.249 |
|  | 1.0 | −54.199 | −50.576 |
|  | 10.0 | −67.062 | −56.673 |
| 8 | 10.0 | −36.967 | −23.373 |
| 7 | 10.0 | −37.065 | −25.868 |
| 5 | 10.0 | −13.374 | −13.787 |
| 9 | 10.0 | −18.880 | −22.129 |
| 3 | 10.0 | −41.438 | −28.513 |
| 10 | 10.0 | −34.891 | −27.830 |
| 2 | 10.0 | −18.151 | −22.514 |
| 1 | 10.0 | −49.137 | −56.058 |
|  | 10.0 | −51.440 | −51.670 |
| 11 | 10.0 | −39.435 | −32.370 |
|  | 10.0 | −27.622 | −34.518 |
| (benzyl)phosphonic acid diethyl ester | 10.0 | −64.417 | −60.724 |
|  | 0.1 | −19.333 | −18.908 |
|  | 1.0 | −25.017 | −29.027 |
|  | 10.0 | −34.457 | −40.081 |
| [(3,4-dimethylphenyl)phosphonic acid dimethyl ester | 10.0 | −31.225 | −35.015 |
| [(3-chlorophenyl)-methyl]phosphonic acid dimethyl ester | 10.0 | −30.224 | −33.802 |
| [(4-chlorophenyl)-methyl]phosphonic acid dimethyl ester | 10.0 | −29.180 | −28.129 |
| 19 | 10.0 | −27.578 | −34.949 |

TABLE 1-continued

DTH GRANULOMA ASSAY

| Compound #/ Compound Name | Dose (mg/kg) | % Change from Control (Wet Weight) | % Change from Control (Dry Weight) |
|---|---|---|---|
| 20 | 10.0 | — | −21.958 |
| 21 | 10.0 | −45.019 | −29.986 |
| 22 | 10.0 | −53.879 | −48.989 |
|  | 0.1 | −29.991 | −17.164 |
|  | 1.0 | −47.467 | −44.341 |
|  | 10.0 | −60.836 | −45.971 |
| 23 | 10.0 | −11.973 | −21.212 |
| 24 | 10.0 | −30.051 | −30.280 |
| 25 | 10.0 | −47.549 | −50.722 |

Representative Compounds of Formula II

The synthesis of compounds of Formula II proceed, generally, as outlined below and, more specifically, in the examples that follow.

Tri- and tetramethyl benzenecarboxylates, or the substituted derivatives thereof, e.g., mono-, di-, or trichlorosubstituted benzenecarboxylate, may serve as starting materials. The carboxylate is reduced first, to the corresponding tri- or tetrahydroxymethyl benzene and in a second step is converted to the tri- or tetrabromide. As an alternative, many of these bromides may be obtained from commercial vendors. In the presence of an organic solvent, the bromide is reacted with excess trialkyl phosphite to provide the tris- or tetrakisphosphonate esters. These products are useful in the method of the invention or may be further modified as described below. These reactions are carried out under ambient to reflux temperature conditions, e.g., 25 to 130 degrees, for a time sufficient to effect as complete a reaction as possible, e.g., from 3 to 48 hours.

The ester groups of the phosphonate may be hydrolyzed by any volatile mineral acid, e.g., hydrochloric or hydrobromic, to the hexa- or octa-acid or the ester groups are selectively removed with bromotrimethyl silane to provide mono-, di-, etc. up to septa-acids. These lesser acids are conveniently separated by reversed phase chromatographic techniques known by those skilled in the art. Esterification of the hexa- or octa-acid and, similarly, the lesser acids, with a second ester group is achieved conveniently with an orthacid or diazoalkane; the diazoalkane, e.g., diazomethane, is believed to be most useful in esterification of sterically hindered acids.

The substituted benzenes of the invention are produced using corresponding bromomethylenes as starting materials using synthetic techniques as described above or, alternatively, from commercial sources. The esterification and alkylation of these compounds is also accomplished following the above procedure.

As each step of the synthesis is completed, the reaction mixture can be treated by conventional chemical processing procedures, e.g., by dilution, solvent partitioning, filtration, concentration, and cooling, to separate the products from the reactants and solvents. The solid compounds of the invention have melting points generally in the range of about 50 to greater than 250 degrees, and thus are easily separated by filtration or centrifugation; oils or liquids are separated by chromatographic methods and further purified by distillation. Solids may be obtained in purer form by recrystallization from hot organic solvents; solids, liquids, and oils may be further purified by chromatographic methods.

The conditions described here and in the examples that follow for the synthesis and purification of the compounds of the invention may be altered depending on the choice of reactants and solvents, the batch size, the degree to which the reaction is to be carried to completion, and other factors of concern to the chemist. Such modifications and alterations are known by those skilled in the art and require no special mention.

By following the preceding description, and without further elaboration, one skilled in the art can utilize the present invention to the fullest extent. The representative examples and demonstrations of utility that follow are merely illustrative, and not limiting, of the disclosure.

Preparation 1 1,3,5-Tris(hydroxymethyl)benzene

A solution of trimethyl 1,3,5-benzenetricarboxylate (8.83 g, 0.035M; Aldrich) in THF (125 mL) is added dropwise over a period of 45 minutes to a stirred mixture of lithium aluminum hydride (3.98 g, 0.105M) and dry THF (150 mL) under a nitrogen atmosphere. The initial phase of the addition results in vigorous reaction and consequently the addition is very slow at first. As the ester solution is added, an orange mass forms when the drops came in contact with the $LiAlH_4$ mixture. A yellowish-green mixture results and is stirred at room temperature. The excess $LiAlH_4$ is quenched carefully by the addition of ethyl acetate and the resulting mixture is acidified with aqueous 2N HCl solution until the pH is <3 and aluminum salts have dissolved. The layers are separated and the aqueous layer is extracted 3 times with additional ethyl acetate and then with methylene chloride. The organic extract layers are dried (sodium sulfate), filtered, and concentrated under reduced pressure to give a white solid (2.98 g, 51%). Recrystallization from acetonitrile-methylene chloride gives the title compound as white crystals (1.13 g) which appear to be hygroscopic when collected by suction filtration. The crystals are dried several days over $P_2O_5$ in a vacuum desiccator after which they have a mp of 76.5°–78° C.

Preparation 2 1,3,5-Tris(bromomethyl)benzene

A solution of thionyl bromide (3.1 mL, 8.3 g, 0.04M) in chloroform (25 mL) is added dropwise over a period of 10 minutes to a stirred slurry of 1,3,5-tris(hydroxymethyl)benzene (Preparation 1, 1.9 g, 0.012M) in chloroform (100 mL). The mixture is stirred at room temperature for four hours during which the solids dissolve into solution. The solution is heated at reflux temperature for 45 minutes, cooled to room temperature, and examined by TLC which shows the reaction is complete. The chloroform and excess thionyl bromide are removed under reduced pressure, leaving a reddish-yellow solid residue. The crude product is chromatographed on a filtration column of gravity silica gel (63–200 mµ, 60 g) in methylene chloride. The column is eluted with methylene chloride and three fractions of 250 mL each are collected. The desired product is eluted in fraction 2 (4.13 g) and is recrystallized from hexane, giving the title compound (3.20 g) as colorless crystals, mp 95.5°–97.5° C. W. Reppe and W. J. Schweckendiek, *Justus Liebigs Ann. Chem.*, 560:1041 (1948) report amp of 94° C.

Preparation 3 1,2,4-Tris(hydroxymethyl)benzene

A dry one liter, 3-necked flask equipped with a nitrogen inlet and dropping funnel is charged with dry THF (200 mL) and $LiAlH_4$ (2.66 g, 0.070M). A solution of trimethyl 1,2,4-benzenetricarboxylate (9.0 g, 0.035M) in THF (125 mL) is added from the dropping funnel over a 20-minute period. This mixture is allowed to stir overnight at room temperature. A TLC on an aliquot (quenched with EtOAc and then shaken with water plus ether) indicated formation of a more polar spot and starting material is gone. The reaction mixture is carefully quenched with ethyl acetate and then acidified to a pH<3 with 2.0N HCl solution until the aluminum salts are dissolved. The layers are separated and the aqueous is extracted with more ethyl acetate (2×). The pooled ethyl acetate layers are dried (sodium sulfate), filtered, and evaporated to yield an oil which is chromatographed on 400 g of 40–63 µm silica gel. The sample is applied in the minimum amount of 50% acetone-methylene chloride and then eluted with 30% acetone-methylene chloride (1 L) followed by 40% acetone-methylene chloride. Fractions which contains 50 mL each are collected. The desired product elutes in fractions 87–114 and is a solid (1.99 g, 0.0118M, 33%). Recrystallization from acetone-hexane gives the title compound (1.12 g) as white crystals, mp 56°–58° C.

Preparation 4 1,2,4-Tris(bromomethyl)benzene

A solution of 1,2,4-tris(hydroxymethyl)benzene (Preparation 3, 1.68 g, 0.010M) in acetonitrile (70 mL) is stirred with triphenylphosphine (12.98 g, 0.0495M). To this is added dropwise over 20 minutes a solution of $CBr_4$ (24.87 g, 0.075M) in acetonitrile (35 mL). A clear yellow solution is observed as the addition proceeds and an exothermic reaction is noted. The reaction is stirred at ambient temperature for 18 hours after which TLC indicates complete reaction. Solvent is removed under reduced pressure. The orange, oily residue is dissolved in methylene chloride and ether is added to crystallize triphenylphosphine oxide. Following removal of the solids by filtration, the residue from the filtrate is plated onto silica gel (50 g, 63–200 µm) from a methylene chloride solution and this silica gel is placed on top of a 400 g column of silica gel which is packed in hexane. The column is eluted with hexane (500 mL), 15% acetone-hexane (B L), and 50% acetone-hexane with collection of 50 mL fractions. Fractions 40–50 contains the title compound (0.566 g, 0.00159M, 15.9%) as an oil.

Compound 26 [1,3,5-Benzenetriyltris(methylene)]trisphosphonic acid, hexamethyl ester A solution of 1,3,5-tris(bromomethyl)benzene (Preparation 2, 3.0 g, 0.0084M) in trimethylphosphite (15 mL, 15.8 g, 0.13M) is heated at reflux temperature for 48 hours. Excess trimethylphosphite is removed under reduced pressure, leaving a white solid residue (4.67 g) which is recrystallized from ethyl acetate to give 1,3,5-benzenetriyltris(methylene)trisphosphonic acid, hexamethyl ester (3.34 g), mp 105.5°–106.5° C.

IR (mull): 1601, 1249, 1239, 1196, 1183, 1175, 1059, 1050, 1041, 1023, 967, 885, 854, 820, 804, 799, 704, 626 $cm^{-1}$. $^1H$ NMR ($CDCl_3$): δ 7.14 (m, 3H, aromatic H), 3.68 (d, 18H, J=10.8 Hz, —$OCH_3$), 3.15 (d, 6H), —$CH_2$—). Mass spectrum $C_{15}H_{27}O_9P_3$ requires 444.0868. Found: 444.0803, 350, 335, 256, 240, 227, 211, 131, 115 m/e. Anal. calc'd for $C_{15}H_{27}O_9P3$: C, 40.55; H, 6.13. Found: C, 40.49; H, 6.24.

Compound 27 [1,2,4-Benzenetriyltris(methylene)]trisphosphonic acid, hexamethyl ester A solution of 1,2,4-tris(bromomethyl)benzene (Preparation 4, 0.532 g, 0.0015M) and trimethylphosphite (15 mL, 0.126M) in dry toluene (25 mL) is stirred and heated at reflux temperature for 80 hours. Solvent and excess trimethylphosphite are removed under reduced pressure and the oily residue is chromatographed over silica gel (50 g, 40–63 µm, 10% $CH_3OH$—$CHCl_3$, 8 mL fractions) using 10% $CH_3OH$—$CHCl_3$ to elute the column. Fractions 16–22 contain the title compound (0.587 g, 0.00132M, 88%), which is a viscous oil.

IR (liquid film): 1248, 1183, 1052, 1029, 860, 818, 617 $cm^{-1}$. Mass Spectrum: $C_{15}H_{27}O_9P3$ requires 444.0868.

Found: 4444.0868, 412, 335, 321,227, 109 m/e. $^1$H NMR (CDCl$_3$): δ 7.19 (m, 3H, aromatic), 3.67 (m, 18H, —OCH$_3$), 3.41 (d, 4H, J=20.6 Hz, —CH$_2$P—), 313 (d, 2H, J=21.1 Hz, —CH$_2$P—). Anal. calc'd for C$_{15}$H$_{27}$O$_9$P$_3$: C, 40.55; H, 6.13; P, 20.92. Found: C, 38.87, 38.14; H, 6.29, 6.38; P, 20.73.

Compound 28 [1,2,4,5-Phenylenetetrakis(methylene)]tetrakisphosphonic acid, octamethyl ester A mixture of 1,2,4,5-tetrakis(bromomethyl)benzene (9.93 g, 0.022M, Aldrich), toluene (75 mL), and trimethylphosphite is heated to reflux temperature (a clear solution results). After 4 hours at reflux temperature, a precipitate forms. An aliquot analyzed by TLC (silica gel 10% methanol-ethyl acetate) after 5.5 hours indicates that all of the starting material has been consumed. The reaction is allowed to cool to room temperature and is left standing at room temperature for 48 hours. The precipitate which forms is collected by filtration and is washed with toluene followed by hexane. A total of 10.68 g of white crystals are obtained, mp 179°–180° C. A 7.5 g portion of the product is recrystallized from acetone-hexane. White crystals of the title compound (5.87 g) are obtained, mp 180.5°–181.5° C. A second crop of crystals (0.96 g), mp 178°–180° C., is obtained. A sample from the first crop is used for analysis.

IR (mull): 1260, 1250, 1183, 1048, 1030, 891,855, 809, 637 cm$^{-1}$. $^1$H NMR (CDCl$_3$): δ 7.17 (s, 2H, aromatic), 3.67 (d, 24H, J=10.5 Hz, —OCH$_3$), 3.39 (d, 8H, J=19.7 Hz, —CH$_2$P—). Mass Spectrum: C$_{18}$H$_{34}$O$_{12}$P$_4$ requires 566.1001. Found: 566.0990, 534, 457.0946, 425, 411, 347, 333, 239, 129, 109, 93 m/e. Anal. calc'd for C$_{18}$H$_{34}$O$_{12}$P$_4$: C, 38.17; H, 6.05; P, 21.87. Found: C, 38.45; H, 5.99; P, 22.06.

Compounds 29–31

The following compounds are prepared by reacting a tris(bromomethyl)benzene or tetrakis(bromomethyl)benzene (synthesized, where appropriate, following the procedures of Preparations 1 through 4), with a trialkylphosphite, as described in the preceding examples. Those skilled in the art recognize that necessary and appropriate adjustments may be required in reaction ratios and conditions and/or chromatography conditions in order to obtain the title compound. Such modifications are well known and within the ability of the skilled artisan.

Compound 29 2-Chlorobenzene-[1,3,5-triyltris(methylene)]trisphosphonic acid, hexamethyl ester Following the procedure of Compound 1, 2-chloro-1,3,5-tris(bromomethyl)benzene is reacted with trimethylphosphite.

Compound 30 1-Fluorobenzene-[2,4,5-triyltris(methylene)]trisphosphonic acid, hexamethyl ester Following the procedure of Compound 1, 1-fluoro-2,3,5-tris(bromomethyl)benzene is reacted with trimethylphosphite.

Compound 31 3-Chlorobenzene-[1,2,4,5-tetrakis(methylene)]tetrakisphosphonic acid, octamethyl ester Following the procedure of Compound 26, 3-chloro-1,2,4,5-tetrakis(bromomethyl) benzene is reacted with trimethylphosphite.

Biological Activity

The utility of the compounds of the invention as a treatment for inflammatory disease is demonstrated by suppression of delayed-type hypersensitivity granuloma (DTH GRA) in mice as described above for Table 1. Assay results for Formula II compounds are shown in Table 2.

TABLE 2

| | DTH GRANULOMA ASSAY | | |
|---|---|---|---|
| Compound # | Dose (mg/kg) | % Change from Control (Wet Weight) | % Change from Control (Dry Weight) |
| 28 | 100 | −50.840 | −39.783 |
|  | 10 | −36.705 | −34.580 |
|  | 10 | −33.058 | −37.841 |
| 27 | 10 | — | −41.023 |
| 26 | 10 | −35.819 | −38.452 |

I claim:

1. A method for treating arthritis or inflammation comprising: administering a therapeutically effective amount of a compound of Formula II

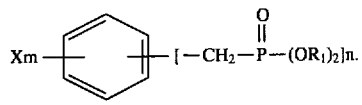

wherein

R$_1$ is independently selected from the group consisting of hydrogen, Na$^+$, K$^+$, NH$_4^+$, (R$_2$)$_4$N$^+$, C$_1$–C$_{10}$ alkyl, —CH$_2$C$_6$H$_5$, —C$_6$H$_5$ or adjacent R$_1$ can be taken together to form —CH$_2$(CH$_2$)$_p$CH$_2$— or —CH$_2$C(CH$_3$)$_2$CH$_2$— (where p is 0–2);

X is independently hydrogen, —OH, —Br, —F or —Cl;

R$_2$ is C$_1$–C$_{18}$ alkyl; and n is 3 or 4 to a patient in need thereof.

2. The method according to claim 1 wherein n is 3.

3. The method according to claim 2 wherein the compound is a) [1,3,5-benzenetriyltris(methylene)]trisphosphonic acid, hexamethyl ester, b) [1,2,4-benzenetriyltris(methylene)]trisphosphonic acid, hexamethyl ester, c) 2-chlorobenzene-[1,3,5-triyltris(methylene)]trisphosphonic acid, hexamethyl ester, or d) 1-fluorobenzene-[2,4,5-triyltris(methylene)]trisphosphonic acid, hexamethyl ester.

4. The method according to claim 1 wherein n is 4.

5. The method according to claim 4 wherein the compound is a) [1,2,4,5-phenylenetetrakis(methylene)]tetrakisphosphonic acid, octamethyl ester, or b) 3-chlorobenzene-[1,2,4,5-tetrakis(methylene)]tetrakisphosphonic acid, octamethyl ester.

\* \* \* \* \*